United States Patent [19]

Altman

[11] 4,233,625
[45] Nov. 11, 1980

[54] TELEVISION MONITORING SYSTEM FOR AUTOMATICALLY ALIGNING SEMICONDUCTOR DEVICES DURING MANUFACTURE

[75] Inventor: Norman G. Altman, Stamford, Conn.

[73] Assignee: Teledyne, Inc., Los Angeles, Calif.

[21] Appl. No.: 957,488

[22] Filed: Nov. 3, 1978

[51] Int. Cl.³ .................. H04N 7/00; G01B 11/00; G01B 9/00; G06K 9/00
[52] U.S. Cl. .................. 358/101; 340/146.3 H; 364/559; 356/400
[58] Field of Search ............ 358/101; 356/399, 400; 340/146.3 H; 364/559

[56] References Cited

U.S. PATENT DOCUMENTS

| | | | |
|---|---|---|---|
| 3,749,830 | 7/1973 | Blitchington, Jr. ................ | 358/101 |
| 3,814,845 | 6/1974 | Hurlbrink et al. ................ | 358/101 |
| 3,903,363 | 9/1975 | Montone et al. ................ | 358/101 |
| 4,131,490 | 12/1978 | Oishi et al. ................ | 358/101 |
| 4,148,065 | 4/1979 | Nakagawa et al. ................ | 358/101 |

Primary Examiner—John C. Martin
Assistant Examiner—Edward L. Coles
Attorney, Agent, or Firm—Gerald Altman; Richard J. Oates

[57] ABSTRACT

In a system for aligning successive configurations of minute semiconductors during manufacture, any selected configuration is carried on a precision X,Y,$\theta$ table, which is under the automatic control of (1) a standard television camera that is subject to conventional geometrical and shading distortions, (2) pattern-recognition and motor-control circuitry that corrects these distortions so that precision alignment is possible, and (3) a monitor including a television viewing screen for supervising the system.

27 Claims, 18 Drawing Figures

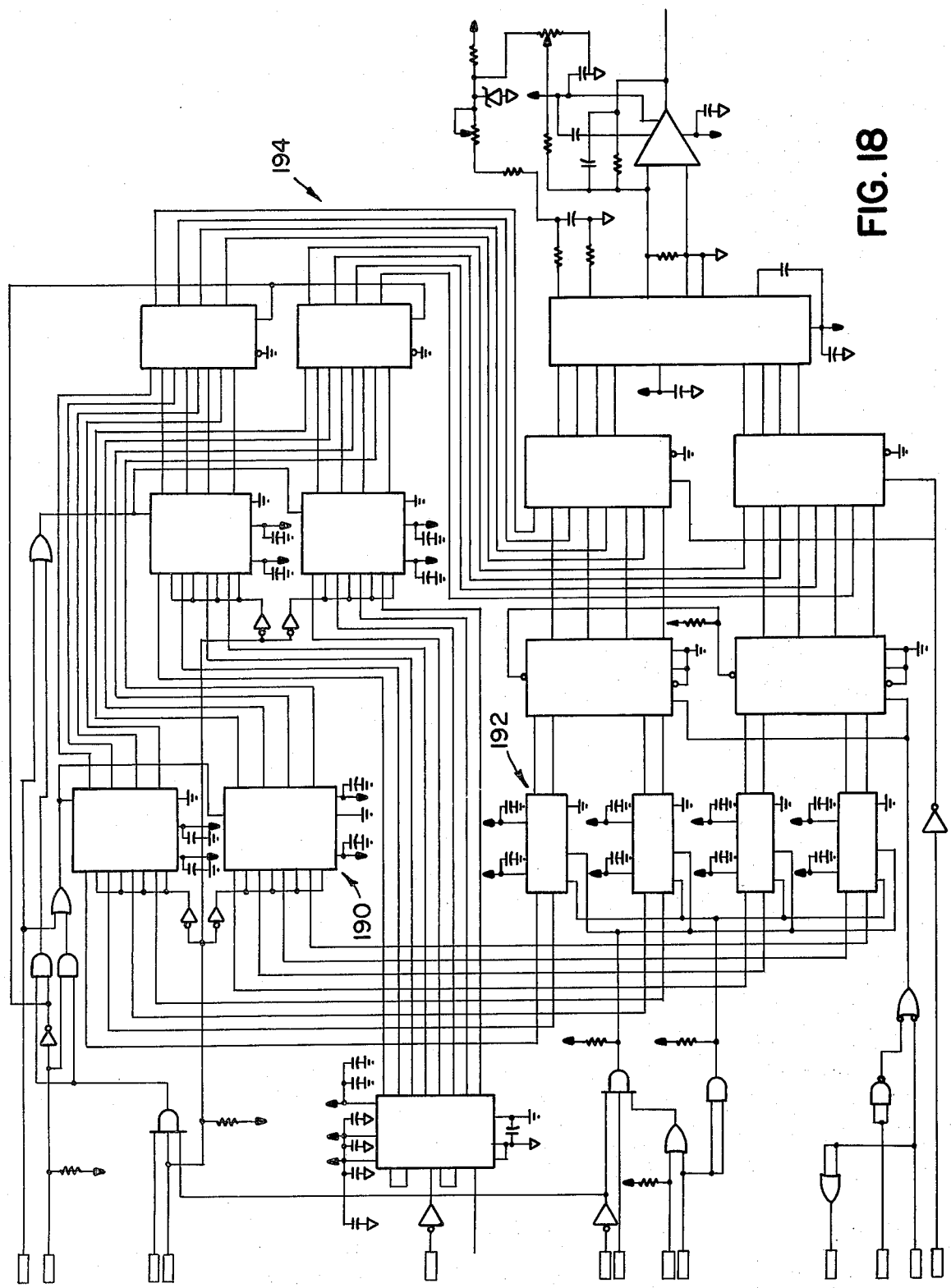

TELEVISION MONITORING SYSTEM FOR AUTOMATICALLY ALIGNING SEMICONDUCTOR DEVICES DURING MANUFACTURE

BACKGROUND OF THE INVENTION

In the manufacture of minute semiconductor devices, it frequently is necessary to align processed wafers or chips (incorporating an array of such semiconductor devices) accurately with respect to some predetermined coordinate system. Such alignment is necessary before the performance of such operations as probing, scribing or sawing wafers and, also, before die bonding and wire bonding chips, in order to separate, manipulate and utilize such semiconductor devices. In the prior art, such alignment usually is accomplished by visual and manual means. An operator, using a microscope or television monitor, visually observes the position of selected elements of the wafer or chip pattern and, using a micromanipulator, positions these selected elements with respect to cross hairs or similar fiducial marks in the microscope or television monitor. Prior attempts to automate this alignment procedure, in order to reduce cost and to improve accuracy, have been unsuccessful.

SUMMARY OF THE INVENTION

The primary object of the present invention is to provide, in a system for aligning a succession of like minute semiconductor configurations, which are characterized by optically presented elements that are perpendicularly related, the combination of a precision X,Y,$\theta$ table for carrying any selected configuration, an ordinary television camera for sensing the selected configuration via a raster of scan lines that are subject to conventional geometrical and shading distortions, a monitor including a television viewing screen for supervising the system, and a pattern-recognition and motor-control sub-system that corrects these distortions so that precision alignment is possible. This control sub-system includes: geometrical compensation circuitry, which senses straight elements of the semiconductor configuration even though they are presented by the television camera as being distorted; shading compensation circuitry, which counteracts uneven shading that is inherent in the raster of scan lines generated by the television camera; and adaptive circuitry involving a cursor display, by which intersecting elements of the semiconductor configuration are memorized during a manual learning mode and utilized during a fully automatic mode.

Other objects of the present invention will in part be obvious and will in part appear hereinafter.

The invention accordingly comprises the system of the present disclosure, together with its components and their interrelationships, the scope of which will be indicated in the appended claims.

BRIEF DESCRIPTION OF THE DRAWINGS

For a fuller understanding of the nature and objects of the present invention, reference is made to the following specification, which is to be taken in connection with the accompanying drawings, wherein:

FIG. 18 is an electrical schematic of another part of the video processor and output circuitry of FIGS. 2 and 3.

DETAILED DESCRIPTION OF THE PREFERRED EMBODIMENT

INTRODUCTION

Generally, the present invention is characterized by:

(1) input information that is provided by an inexpensive commercial television camera; and (2) an alignment capability that is very broad spectrum, i.e. capable of working with almost any type of semiconductor and with almost any type of alignment mechanism.

The use of an inexpensive, low performance television camera system introduces several major problems, for which the system of the present invention provides reliable, economically feasible solutions. These problems are:

(1) scan distortion;

(2) instability of raster size and position;

(3) variation in DC level and signal sensitivity over the field of view;

(4) signal amplitude distortion due to AC coupling; and (5) smear and similar distortions due to the long delay time of the photosensitive target.

There are, however, many advantages to using a television camera to provide the input information to the system. These advantages are:

(1) minimal monitor cost;

(2) a simple man-machine interface by which the system can be "taught", i.e., adapted for association with different elements of the semiconductor devices for alignment purposes; and (3) retrofitting, of existing manually operated alignment devices with an automatic capability, which can be accomplished at minimum cost, if a television monitor already is present.

The following discussion of the alignment system of the present invention is limited specifically to the alignment of wafers. The application of this system to chip alignment will be obvious to persons skilled in the art. Wafers are manufactured by a step-and-repeat procedure, which generates a two-dimensional array of information on a surface, the wafer consisting of discrete rectangular areas separated from each other by a grid of linear boundaries. These boundaries, which range normally from a few thousandths of an inch wide to as much as ten thousandths of an inch wide, commonly are called "thoroughfares", because they resemble a layout of urban streets.

THE BLOCK DIAGRAM OF FIG. 1

Figure 1:
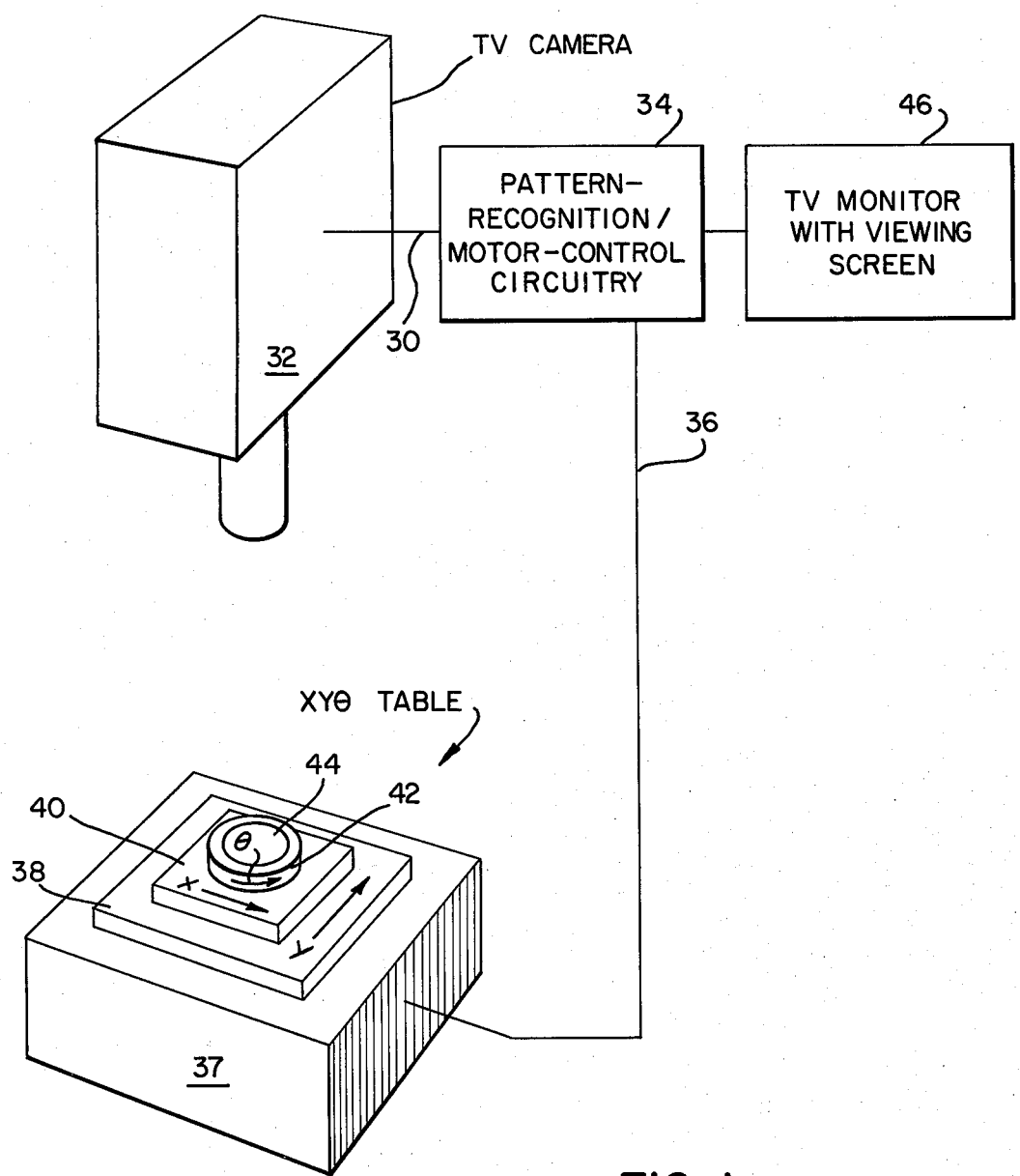
FIG. 1 is a schematic diagram, partly mechanical and partly electrical, illustrating the general operation of a system embodying the present invention.

A general block diagram of the present invention is shown in FIG. 1, wherein video signals 30, carrying information from a television camera 32, are processed in a suitable pattern recognition/motor-control sub-system 34. Control signals 36, which are generated thereby, feed into stepping motors (not shown), which control a mechanical positioning table 37. Table 37 includes a set of beds that provide Y motion 38, X motion 40, and $\theta$ motion 42. A wafer to be aligned, as shown at 44, is mounted on the X,Y,$\theta$ table structure, which is illuminated by a light source (not shown) so that the wafer can be viewed by television camera 32. A monitor 46 provides a visual display, of the information in the television camera's field of view, on a television screen.

Since television camera 32, television monitor 46, and X,Y,$\theta$ table structure 37, individually, are well known in the art, only pattern-recognition and motor-control sub-system 34 is described below in detail.

SUMMARY OF THE FUNCTIONS OF THE SYSTEM OF FIG. 1

The technique implemented by the system of FIG. 1 utilizes certain geometric features that are universal in all wafers, namely, the presence of border spaces, or "thoroughfares", between adjacent semiconductor devices on the wafer. These thoroughfares serve as reference elements for alignment of the wafer during (1) an "instruction" mode, in which an operator instructs the system regarding which edges of the thoroughfares are suitable for precise alignment, and (2) an "automatic" mode, in which the system itself senses these thoroughfares on a succession of wafers and aligns these wafers with respect to the system for processing.

After a wafer on X,Y,$\theta$ table 37 has been moved into position manually or automatically so that an area near the center of the wafer is in the field of view of television camera 32, the following general functions are performed by the system. For reasons to be explained below, in the present system, the X direction is 45° clockwise with respect to true vertical and the Y direction is 45° counterclockwise with respect to true vertical.

(1) X motion is commanded until a vertical thoroughfare is sensed in the field of view by X sensing circuitry. This vertical thoroughfare thereby is centered coarsely (within a few thousandths of an inch).

(2) A large Y motion is commanded until an area near the edge of the wafer is seen in the field of view. At this position, $\theta$ error which appears as X displacement, is sensed by the X sensing circuitry, and is corrected by $\theta$ motion of X,Y,$\theta$ table 37.

(3) A second large Y motion is commanded in the sense opposite to that of (2) above, returning the center of the wafer to the field of view.

(4) Additional Y motion is commanded until a horizontal thoroughfare is sensed in the field of view. At this time, the intersection of vertical and horizontal thoroughfares seen in the field of view is centered coarsely. Edges near the intersection, characteristics of which have been memorized during the instruction cycle, have been positioned to within a few thousandths of an inch of a reference point and are now used to fine align the intersection by precise X and Y motions.

(5) A large Y motion is commanded to bring an area near the edge of the wafer into the field of view. Function (4) is repeated except that, during fine alignment to correct for apparent Y and X displacements of this intersection, Y and $\theta$ motions are commanded, providing fine $\theta$ correction at the edge of the wafer.

(6) Functions (3) and (4) are repeated. If the intersection in the field of view is permitted to be used for alignment in accordance with the learning cycle, the alignment is complete.

(7) If, during the learning cycle, the system has been instructed to memorize a specific intersection for final alignment which intersection is defined by a unique memorized pattern, then, after the wafer is returned to the center, the surrounding area is scanned by a search pattern that follows the thoroughfares in an optimal path, sensing each intersection until the specific intersection is found. Then function (4) is repeated, completing the alignment.

Figure 4:
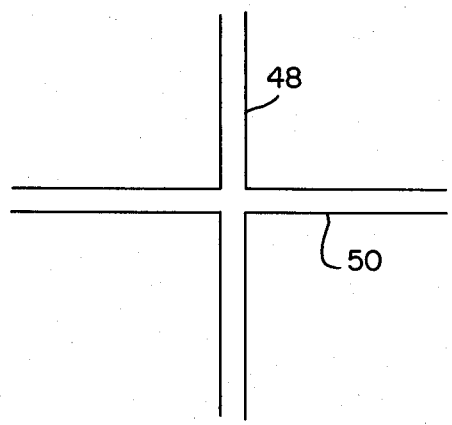
FIG. 4 illustrates certain principles of the present invention in reference to an area of a semiconductor wafer that is being processed.
Figure 5:
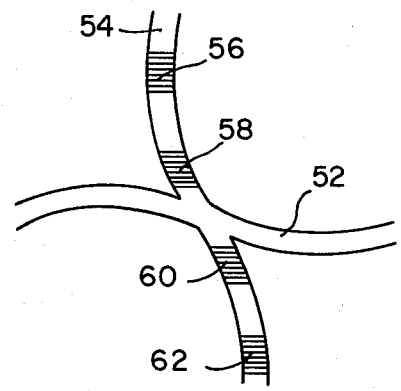
FIG. 5 illustrates other principles of the present invention in reference to the semiconductor wafer area shown in FIG. 4.

THE FIELD OF VIEW—FIGS. 4 and 5

Figure 2:
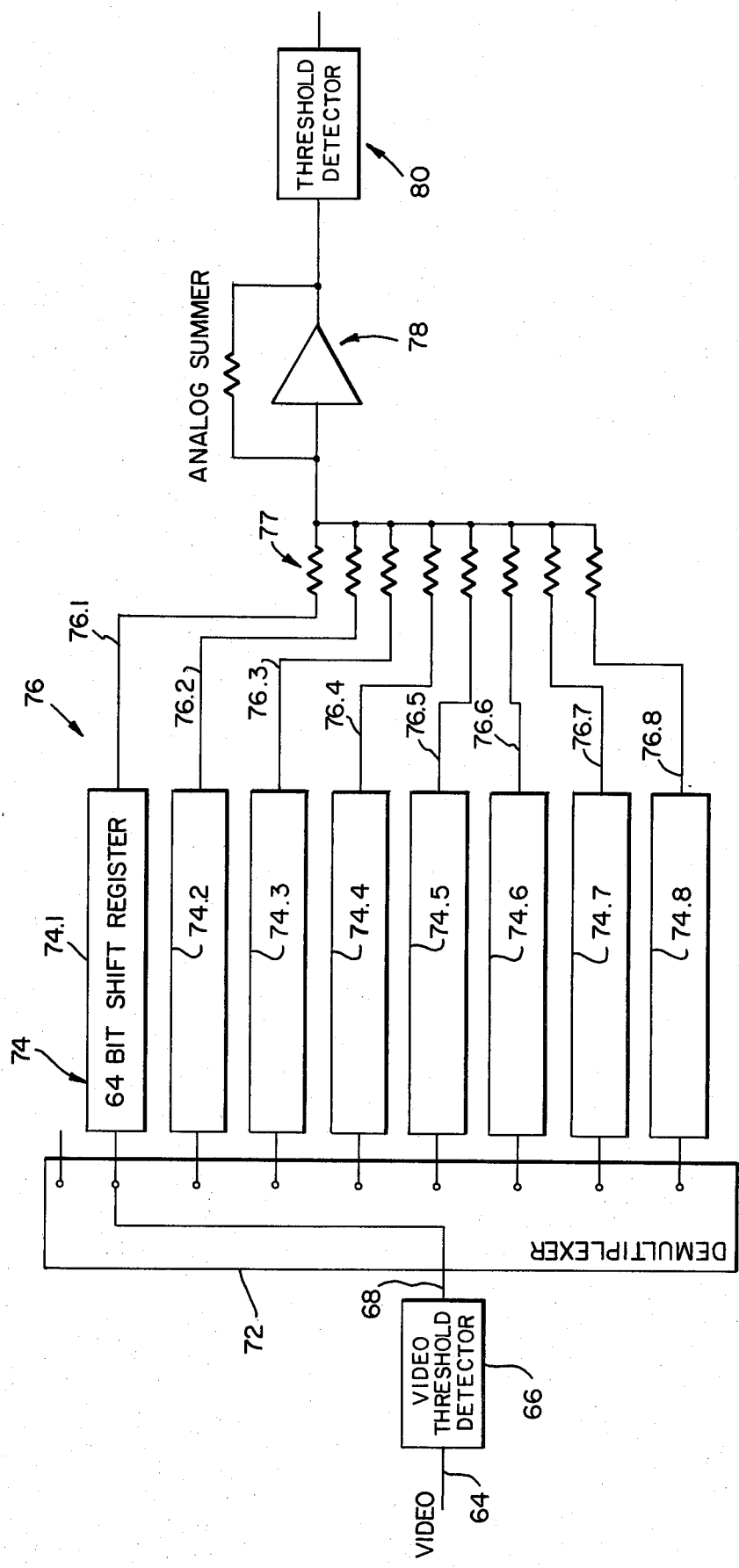
FIG. 2 is a block diagram of the pattern-recognition and motor-control sub-system of the system of FIG. 1.
Figure 3:
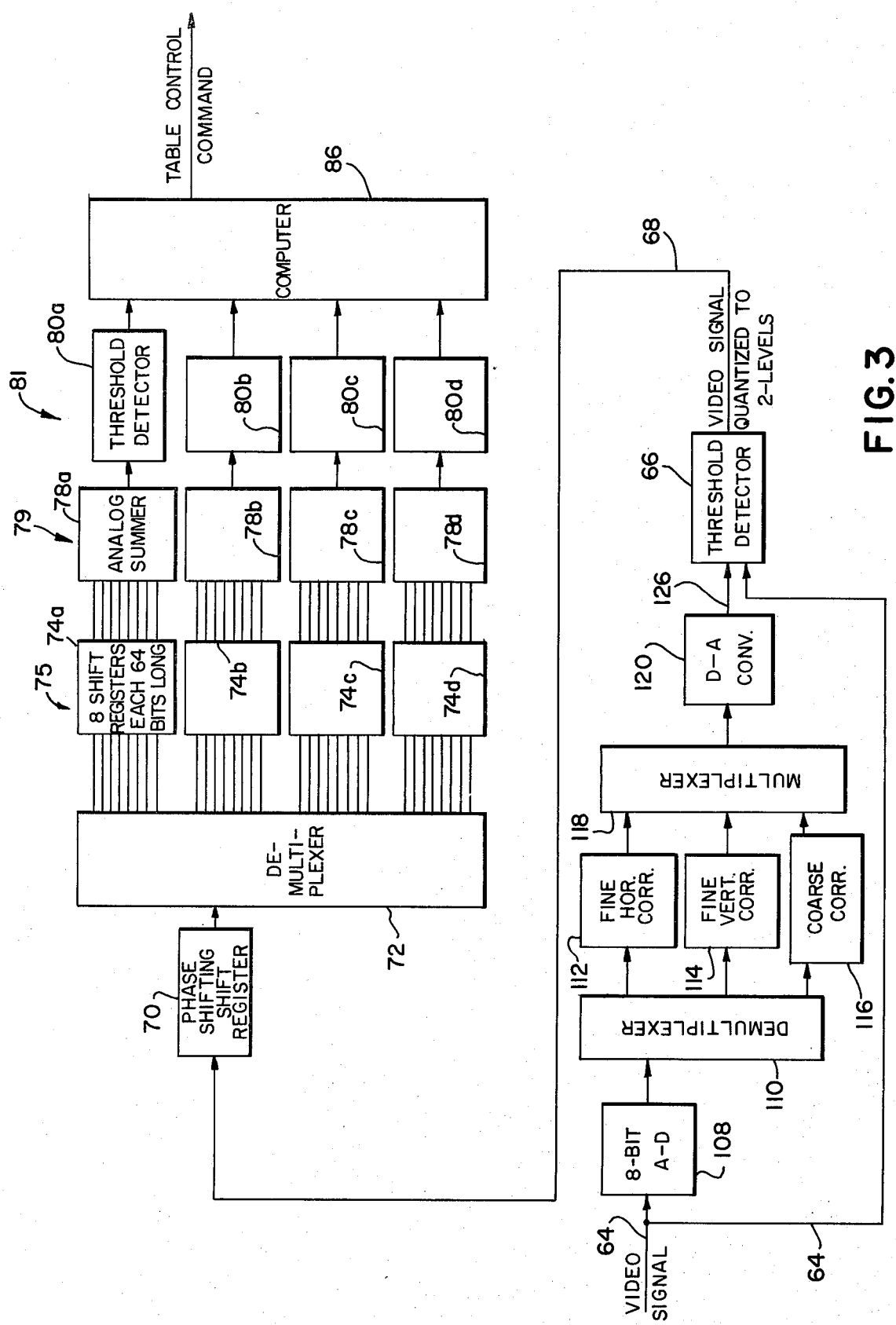
FIG. 3 is an electrical schematic of a part of the block diagram of FIG. 2.

In order to understand the specific operation of the circuits of FIGS. 2 and 3, consider an intersection of vertical and horizontal thoroughfares. FIG. 4 shows how this intersection would appear on a monitor, set up for manual alignment, if there were no distortion in the camera/monitor system. Vertical thoroughfare 48 and horizontal thoroughfare 50 are seen as straight bands intersecting perpendicularly. A video signal from a television camera generating this display would contain information that could be used easily to identify the two thoroughfares. In the present embodiment, the wafer is illuminated obliquely so that the thoroughfares appear dark against a light background. The horizontal thoroughfare would appear as a short series of contiguous long dark scan lines. The vertical thoroughfare would appear as a long series of short dark scan line segments, each such scan line segment occurring on adjacent scan lines at the same elasped time with respect to the start of the video scan line of which it is a part. Information appearing on the set of n scan lines in the foregoing way can be sensed and detected by a number of standard techniques, one of the most common of which is memory masking.

However, when the display of a practical system is examined, the thoroughfares are no longer straight and do not intersect perpendicularly. The geometric distortions of the camera/monitor system introduces curves in the horizontal and vertical thoroughfares and nonperpendicularity in their intersections, as shown in FIG. 5 at 52, 54. In a conventional commercial camera/monitor system that is used for manual alignment, such distortion commonly is 10% or higher. FIG. 5 shows the appearance of the thoroughfares on a monitor where the peak-to-peak system distortion is about 10%. It easily can be seen that there is not even one video scan line, which will be all dark due to falling within a horizontal thoroughfare. Thus, sensing and detecting a horizontal thoroughfare with so much geometric distortion requires a relatively sophisticated degree of pattern recognition. Although this degree of pattern recognition easily is accomplished by a human with little or no training, it is beyond the capabilities of cost effective automatic alignment systems of the prior art.

The present invention adopts a relatively simple and inexpensive processing technique for recognizing a thoroughfare, which is considered as being vertical, and aligning with respect to it, even with much higher distortions than those shown in FIG. 5. As will be explained later, the two intersecting thoroughfares are considered alternately as vertical during the alignment sequence. For ease of understanding, only one thoroughfare, in vertical orientation, will be considered now. This technique involves examining a set of band segments along the length of vertical thoroughfare 54. A set of four such band segments 56, 58, 60, 62 are shown. For these band segments to indicate the presence of a vertical thoroughfare, each must occupy a video scan position which overlaps in time the video scan position of the band above it (if there is one) and the video scan position of the band below it (if there is one). Thus, in FIG. 5, band segments 56 and 58 must time overlap on their scan lines, and band segments 60 and 62 must have time overlap on their scan lines. But, no time overlap is required between band segments 56 and 62. This last non-constraint allows the vertical thoroughfare to be found even in the presence of large geometric distortion or large angular rotation.

THE EXAMINATION BAND CIRCUIT—FIGS. 3 AND 6

Pattern recognition control circuit 34 of FIG. 1, details of which are shown in FIG. 2, is designed to implement the sensing of band segments 56, 58, 60, 62. Since the nature of the thoroughfares is such that, even when they should appear entirely dark, they may include mirror bright regions, the sensing procedure must be able to recognize "almost dark" regions as well as "completely dark" regions. The sub-circuit of FIG. 3, which is one of four like sub-circuits of FIG. 2, is designed to implement this recognition function.

Figure 6:
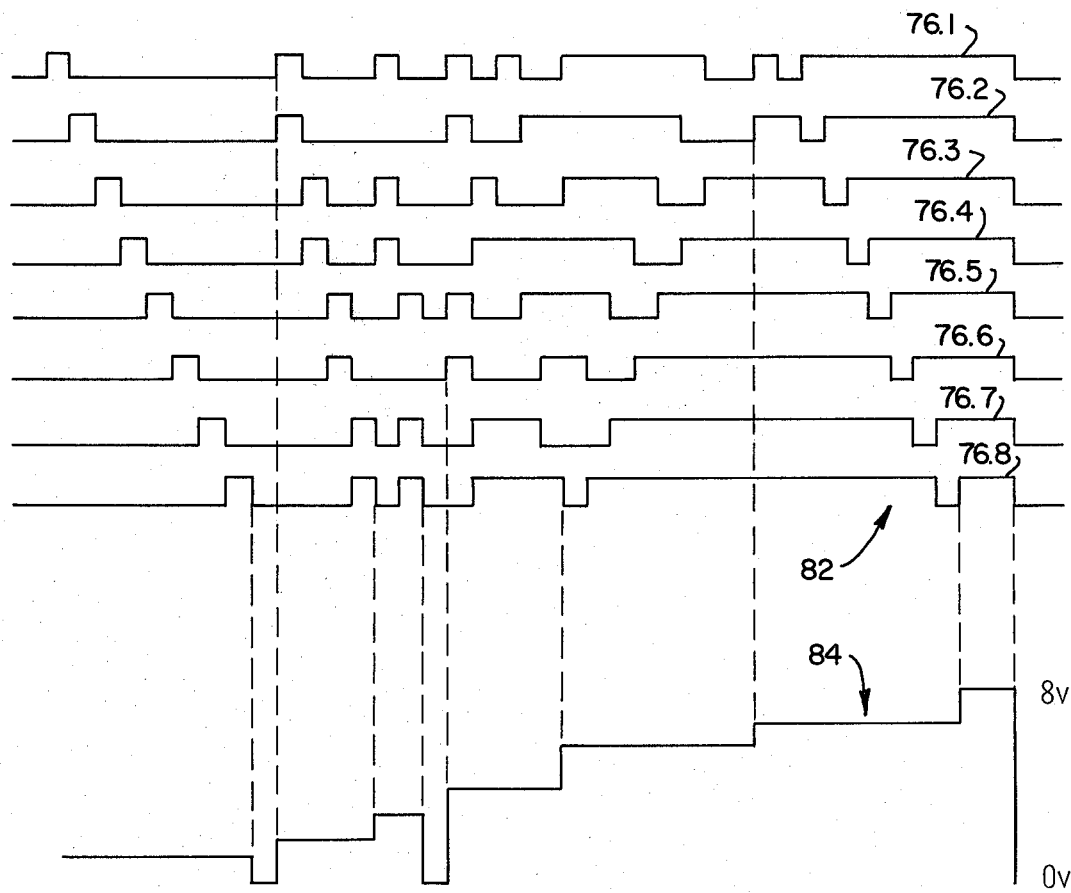
FIG. 6 shows wave forms generated by the circuit of FIG. 3 in reference to the semiconductor wafer area shown in FIG. 4.

Referring now to FIGS. 3 and 6, a video signal 64 is processed by a threshold detector 66 to generate a standardized signal 68, characterized by a two level logic train, with 0 volts chosen arbitrarily to represent dark, i.e., darker than a selected reference level, and +5 volts chosen arbitrarily to represent light, i.e., lighter than a selected reference level. This quantized video signal 68 is fed (FIG. 2) through a phase-shifting shift register 70 to a demultiplexer 72, which is shown in FIG. 3 as a 9-position solid state switch. The functions of shift register 70 and demultiplexer 72 will be described below. With a 0.96 megahertz clock, all of video information 68 from a single horizontal television scan line is stored in one of a group 74 of eight 64 bit shift registers designated 74.1 to 74.8. In the system as illustrated in FIG. 2, there are four such groups of eight 64 bit shift registers. Demultiplexer 72 operates to feed the quantized signal 68 for one horizontal scan line into a selected one of shift registers 74. These shift registers 74 are connected to recirculate on command so that, once a register is loaded by demultiplexer 72, a full horizontal line of video information then is recirculating within it. The recirculation, controlled by the master 0.96 megahertz clock, ensures that all of the video information being recirculated is maintained in time synchronism with the horizontal sweep rate. The circuit is such that the quantized video representations of eight horizontal sweep lines are stored respectively in the eight shift registers of group 74. The condition of the eight shift registers thereby represents a sequence of digitized scans of a section of the television field of view, this sequence of scans intersecting a representation of a vertical thoroughfare at band segments 56, 58, 60 or 62, FIG. 5. In other words, all of the information for sensing and detecting the intersection of a set of eight scan lines with a vertical thoroughfare is present simultaneously in the group 74 of eight recirculating shift registers shown in FIG. 3. And four such groups of eight recirculating shift registers contain all the information for sensing and detecting four band segments 56, 58, 60, 62 of a vertical thoroughfare 54.

In actual practice, there usually are a few bright points in any dark band segment. In consequence, a recognition decision during sensing of a thoroughfare must be based on majority logic rather than on a simple requirement that there be a dark area represented in all of the scan lines at the same horizontal reference position. In the illustrated embodiment, the eight outputs 76 (FIG. 3) individually designated 76.1 to 76.8, from the eight shift registers of group 74 are fed through a group of resistors 77 to an analog summer 78, which feeds a threshold detector 80. Analog summer 78 and threshold detector 80 generate decision signals on the basis of majority logic as follows. The analog summer is a standard operational amplifier connected in the classic summing mode so that the output from each of the shift registers of group 74 is given a weight (referenced to the output of the summer) of one volt. Therefore, if a totally dark region is scanned, the information stored in the eight recirculating shift registers will be such that each output is zero volts and the output of summer 78 is zero volts. A representative set 82 of eight input wave forms, representing signals 76.1 to 76.8, is shown in FIG. 6, together with a wave form 84, representing the resulting output. Note specifically that output 84 is zero only if all inputs are zero. Output 84 is one volt if any one input is non-zero, that is, if any one input is a logic ONE. If any two inputs are non-zero, i.e., if they are logic ONE's, output 84 is 2 volts. Three input logic ONE's produce an output 84 of three volts. Following the circuit of FIG. 3 and the wave forms of FIG. 6, it is seen that the reul exemplified above results in a 7 volt output when there is only one logic ZERO input, and in an 8 volt output when there are only logic ONE inputs.

Thus, with threshold detector 80 set to "fire" at 0.5 volts, it will fire only when all inputs to summer 78 are logic ZERO's; with the threshold detector set at 1.5 volts, it will fire when at least 7 of the eight inputs are logic ZERO's; and with a setting of 2.5 volts, it will fire when only six or more inputs are logic ZERO's. With four circuits of the type shown in FIG. 3, the four band segments 56, 58, 60, 62 of FIG. 5 can be examined and an output can be generated for further processing, whenever there is an indication of a vertical thoroughfare at whatever majority level decision is desired.

SENSING OF VERTICAL AND HORIZONTAL THOROUGHFARES FIGS. 2, 7, 8 AND 11

As shown in FIG. 2, demultiplexer 72 feeds a set 75 of four groups of shift registers 74a, 74b, 74c, and 74d, each of which corresponds to group 74 of FIG. 3. Set 75 feeds at set 79 of analog summers 78a, 78b, 78c, and 78d, each of which corresponds to analog summer 78 of FIG. 3. Set 79 feeds a set 81 of threshold detectors 80a, 80b, 80c, and 80d, each of which corresponds to threshold detector 80 of FIG. 3.

In the present configuration, the outputs of the set 81 of four threshold detectors serve as inputs to a simple microcomputer 86, which stores the information in memory in the form of an array of 4×64 bits. This array is examined by standard computer masking circuitry to determine whether the overlap requirements listed above are met. If they are, over a wide enough area in the array to represent a thoroughfare, when the detection process reports that a vertical thoroughfare has been found and reads out the coordinates within the 4×64 bit array of microcomputer 86. In correspondence with these coordinates, a command is generated to move the wafer table so that the vertical thoroughfare is centered within the field of view. With the magnifications normally used, this centering can be accomplished to within a few thousandths of an inch. This centering is sufficiently accurate to allow initiation of the fine alignment procedure described below.

The above technique is fully adequate for sensing a distorted and rotated vertical thoroughfare and for determining its position, but will not sense a horizontal thoroughfare. The technique for sensing a horizontal thoroughfare is desired below.

Figure 11:
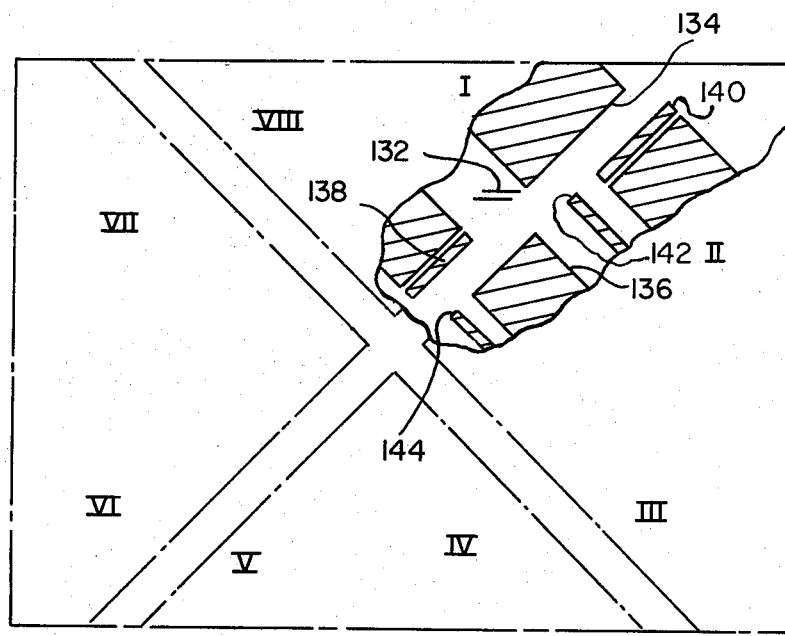
FIG. 11 illustrates other principles of how an area being sensed by the television camera is processed by the circuitry of FIGS. 2 and 3.

In accordance with the present invention, the video information is controlled so that horizontal thoroughfares also are processed in the manner described above for vertical thoroughfares. For this purpose, the perpendicularly intersecting thoroughfares are presented to television camera 32 at 45° angles with respect to vertical and horizontal coordinates defined by television camera 32. Thus, on monitor 46, as shown in FIG. 11, "vertical" thoroughfares initially are seen as extending from lower left to upper right and "horizontal" thoroughfares as extending from lower right to upper left. Control circuitry 34 (FIG. 1) operates to rotate these thoroughfares electronically so that each, when being examined, appears to the recirculatory shift registers 75 as vertical. That is, the "vertical" thoroughfares are electronically rotated counterclockwise 45° to appear vertical and the "horizontal" thoroughfares are electronically rotated clockwise 45° to appear vertical.

Figure 7:
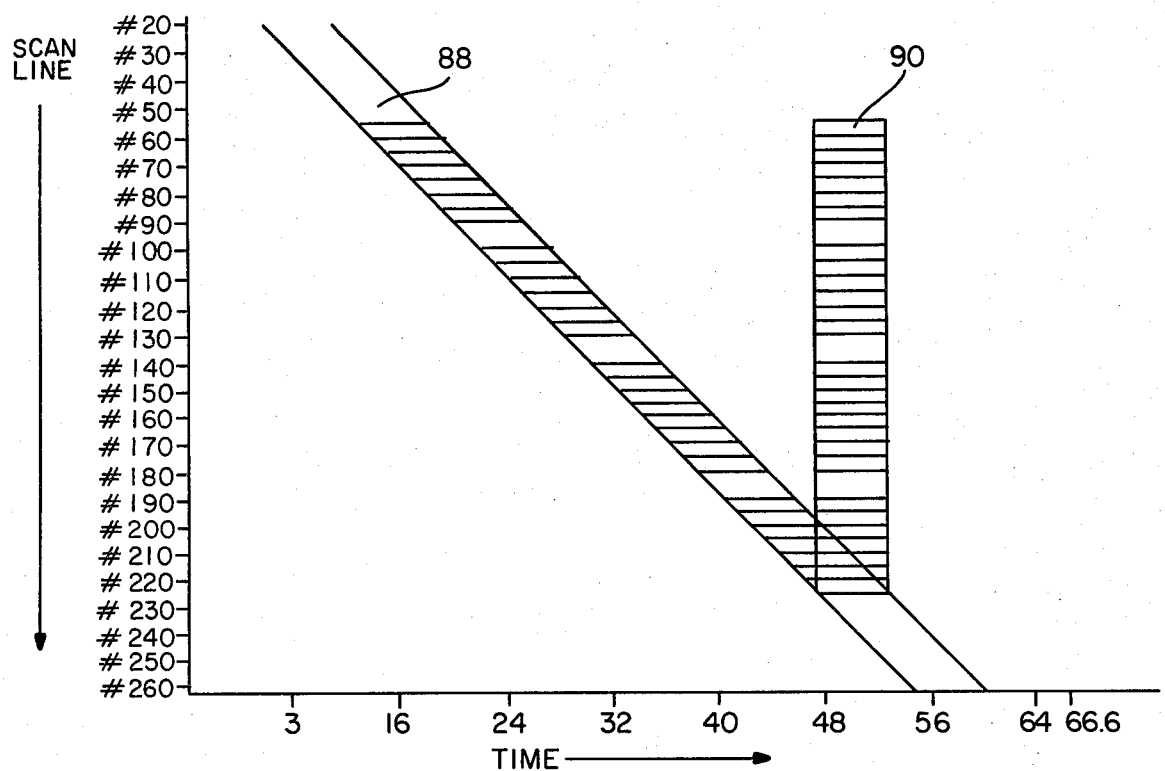
FIG. 7 illustrates certain aspects of the operation of the circuitry of FIGS. 2 and 3.

The circuitry of FIG. 2 for accomplishing this electronic rotation now will be described in reference to the graphical representations of FIGS. 7 and 8. In FIG. 7, a horizontal thoroughfare 88 is shown as it appears on the monitor at 45° with respect to the coordinates of the television camera. A portion of this thoroughfare (the portion which has been sensed as having band segments 56, 58, 60, 62, FIG. 5) is rotated electronically by phase shifting circuitry to be discussed below, to appear to the recirculating shift register memories as if it were in orientation 90 of FIG. 7. In similar fashion, the "vertical" thoroughfare 92, shown in FIG. 8 as it appears on the monitor in FIG. 8, has its video representation rotated by the phase shifting circuitry to appear to the circulating shift register memories as if it were in orientation 94 of FIG. 8. The circuitry is such that the rotation, in both cases, is effected electronically only and does not appear visually on monitor 46. On the monitor, the vertical thoroughfare continues to extend diagonally from lower left to upper right and the horizontal thoroughfare continues to extend diagonally from lower right to upper left.

Further examination of FIG. 7 will facilitate an understanding of how electronic rotation is accomplished. A standard television screen provides two interlaced fields of scan lines to produce a full picture frame. The illustrated system utilizes only one of these fields. This field consists of 262 horizontal scan lines, of which 18 are blanked. In FIG. 7 (as well as in FIG. 8), the horizontal scan lines are designated #1 to #262, the blanked scan lines being designated #1 through #18. Thus the unblanked field of view, for the fields to be processed, contains scan lines #19 to #262. Band segments 56, 58, 60, 62, FIG. 5, are generated by examining:

for band segment 56—scan lines #55,#60, #65,#70, #75,#80,#85,#90;

for band segment 58—scan lines #100,#105,#110,#115, #120,#125,#130,#135;

for band segment 60—scan lines #145,#150,#155,#160, #165,#170,#175,#180; and for band segment 62—scan lines #190,#195,#200,#205, #210,#215,#220,#225.

Each of these 32 scan lines is quantized to two logic levels, as discussed above, by threshold detector 66. However, instead of feeding the quantized video signal 68 directly through demultiplexer 72 into recirculating shift registers 76, as was discussed above, it is fed through shift register 70 (FIG. 2) which introduces a time delay. By shifting the digital information into shift register 70 in "real time" (i.e., simultaneously with the creation of the information by the horizontal scan that generated it) and then delaying shifting out of the information by a predetermined period of time, an additional phase shift or time delay is introduced into the information for each successive horizontal video scan line. With this time delay shift register 70, the quantized video signal from each horizontal scan line is delayed the precise amount necessary to rotate the information it represents (FIG. 7) from the 45° inclination shown at 88 to the vertical configuration shown at 90. This rotation requires that the scan lines of video information be delayed different amounts, with scan lines #55 being delayed the maximum amount and scan line #225 not being delayed at all.

Having introduced this delay by means of shift register 70, the information in any recirculation shift register 74 is properly "rotated" so that a horizontal thoroughfare 88 (FIG. 7) in the field of view will generate a group of logic ZERO's that travel in time sequence as if they had been initiated by a vertical thoroughfare and will generate identifiable voltages for a "vertical" thoroughfare on the outputs of summers 78. These voltages trigger threshold detector 80, which thereby transmits to microcomputer 86 signals, by which the microcomputer can recognize the presence and rotated position of a horizontal thoroughfare in the field of view.

Figure 8:
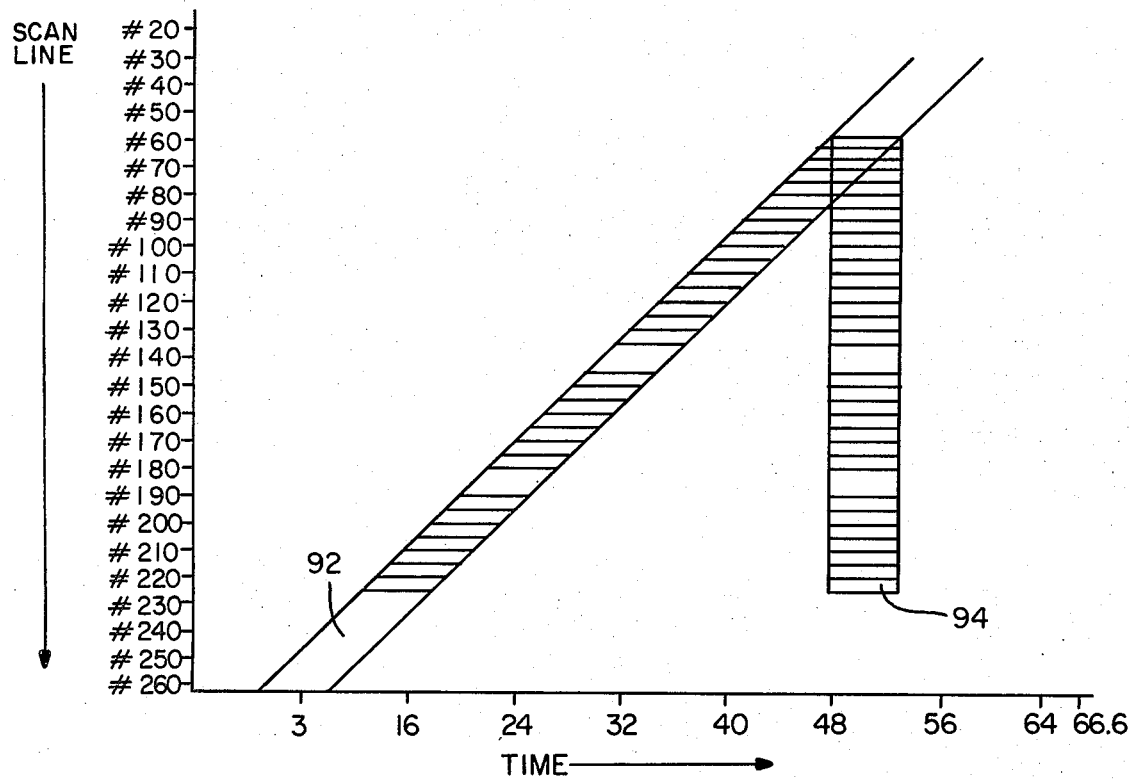
FIG. 8 illustrates other aspects of the operation of the circuitry of FIGS. 2 and 3

The technique for processing the information representing a true vertical thoroughfare, as shown in FIG. 8, is analagous to the technique for processing information representing a horizontal thoroughfare, as shown in FIG. 7. In FIG. 8, the video information in scan line #55 has no delay and that in scan line #225 has maximum delay. It will be apparent that the two types of delays, required to properly rotate the vertical and horizontal thoroughfares, cannot be introduced simultaneously. The two types of delays must be produced sequentially. First, one of the two intersecting thoroughfares is sensed and its distance from center is found and corrected. Then, the other of the two intersecting thoroughfares is sensed and its distance from center is found and corrected.

CORRECTION OF SHADING DISTORTION FIGS. 2, 9 AND 10

Figure 9:
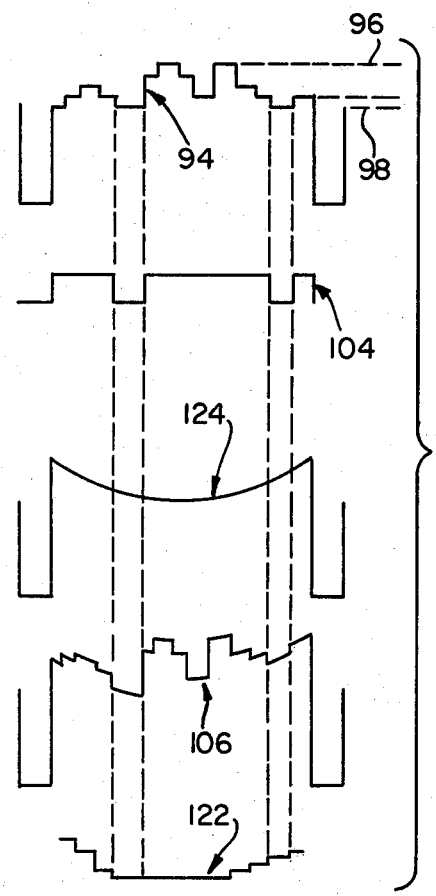
FIG. 9 shows wave forms generated by scan lines of the television camera and processed by the circuitry of FIGS. 2 and 3.

The processing techniques described above require distinguishing the dark areas in the field of view from the light areas by examining the video signal. The dark areas then are represented by logic ONE's. In an idealized video signal 94, as shown in FIG. 9, resulting from one horizontal scan line, separating dark levels 96 from light levels 98 with respect to any arbitrary threshold level 100 is easily done. In quantized video signal 104, a logic ZERO represents all portions of video signal 94 which fall below the threshold 100 and a logic ONE represents all portions of video signal 94 which are above the threshold. However, the video signal generated by one horizontal scan line, in actual practice, departs greatly from wave form 94 and, more closely, is represented by wave form 106, which is a combination of idealized video signal 94 and the shading that is inherent in a vidicon tube.

With shading magnitude that commonly is a large fraction of video signal magnitude, and in some cases equals the peak video signal magnitude, there is no threshold level that can be chosen to separate the video signal into two parts representing the dark and light parts of the object being scanned. It is necessary to introduce shading correction. For this purpose, the present embodiment includes an analog-to-digital (A/D) convertor 108 (FIG. 2), a demultiplexer 110, three first-in-first-out (FIFO) memories 112, 114, and 116, a multiplexer 118, and a digital-to-ananlog (D/A) convertor 120. With the television camera looking at a featureless object, this circuitry generates a memorized shading level signal 122 (FIG. 9), which is a quantized version of the shading signal input 124 from the television camera. Quantized video shading signal 122 (on line 126 of FIG. 2) serves as the threshold level for threshold detector 66. In this way, the quantized signal at 126 corrects for shading. Any video level of shaded video signal 106 (FIG. 9) that falls below the corresponding level of threshold signal 122 represents a dark area on the object being scanned. Any video level that exceeds the corresponding threshold level represents a bright area. These dark/bright decisions, as made by threshold detector 66, result in a quantized signal that is independent of shading level 124.

Quantized reference signal 122 is generated when television camera 32 views a neutral, evenly illuminated, dark, dull object. Video signal 64 so generated is digitized by A/D converter 108 and is fed through demultiplexer 110 into one of three FIFO memories 112, 114, 116. These memories are in the form of shift registers, which are 8 bits wide in correspondence with the 8 bit structure of A/D convertor 108. Consider first only memory 116 for coarse correction. The information fed into this memory represents the shading levels for only those 32 scan lines which have been chosen in correspondence with band segments 56, 58, 60, 62. Since the video signals of the scan lines of these band segments are utilized for searching, detecting, and determining the positions of the thoroughfares, it is only these scan lines that require shading correction for coarse alignment. Limiting the shading correction to these 32 lines results in a relatively small memory 116 for shading correction during coarse alignment.

The information circulating through memory 116 is maintained in synchronism with the scan rate of television camera 32 by the system clock. Thus, whenever a scan line across one of band segments 56, 58, 60, 62 is generated by television camera 32, the appropriate shading correction signal, maintained in synchronism with this scan line, is fed through multiplexer 118 to D/A converter 120. The output of the D/A converter is quantized shading correction signal 122, which is fed to threshold detector 66 as the reference threshold signal.

Figure 10:
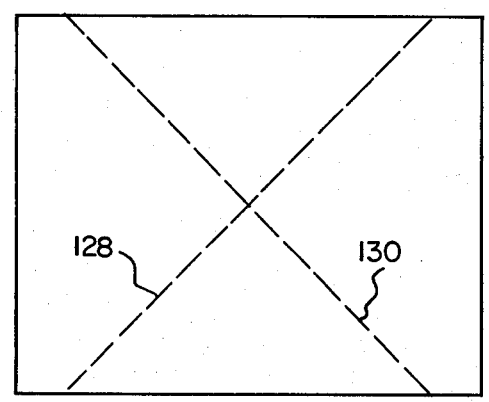
FIG. 10 illustrates certain principles of how an area being sensed by the television camera is processed by the circuitry of FIGS. 2 and 3.

The shading correction during fine alignment is similar to the shading correction discussed above with the following differences. Fine alignment is effected in a very restricted area of the field of view since fine alignment is initiated only after coarse alignment is completed. Therefore, since fine alignment is in response only to information along the edges of a coarsely aligned thoroughfare, shading correction for fine alignment is required only parts 128 and 130 of FIG. 10. This shading correction is provided by means of FIFO memories 112 and 114, FIG. 2, in precisely the same way that shading correction in coarse alignment is provided by means of FIFO memory 116. Since the rotation procedures depicted in FIG. 7 and 8 cannot be accomplished simultaneously, the fine corrections are performed sequentially. To provide proper shading correction for these sequential operations, information sequences representing the shading correction for regions 128, 130, FIG. 10, are stored separately in FIFO memories 112, 114, respectively, and retrieved at the proper time in proper synchronism with the scan lines under control by the system clock. At the proper time, these FIFO memories provide reference signals via multiplexer 118 and D/A converter 120 to threshold detector 66.

FINE ALIGNMENT—FIG. 11 THE LEARN AND AUTOMATIC MODES

To ensure accuracy and repeatability of alignment to a required level of 0.0002 inch, positioning which depends on the geometric centroid of a thoroughfare is not adequate. The presence of simple blemishes, scratches or scribe marks in the thoroughfare will defeat this technique. The present invention senses edges of a thoroughfare as reference marks for fine alignment. Specifically, positioning two such edges, one along a vertical thoroughfare and the other along a horizontal thoroughfare, ensures that the intersection formed by these two thoroughfares is properly aligned.

The edges selected for fine alignment must meet several requirements:

(1) They must be well within the field of view after coarse alignment;

(2) They must extend several thousandths of an inch along the thoroughfare; and (3) They must represent an edge of a feature that is several thousandths of an inch wide.

The latter two requirements ensure that displacements of the pattern, due to lack of precision in the coarse alignment procedure, do not confound the fine alignment procedure. Such confounding will result if the edge that has been memorized during the initial "learn" mode (to be described below) is not within the small area being scanned to provide information for the fine alignment. To ensure that the edges chosen do indeed meet these requirements, the selection is made by the operator during the learn mode, as follows. The oeprator manually positions the first wafer of a group to be aligned, using manual controls that are connected in parallel with the automatic alignment system. In making this manual alignment, the operator ensures that, if a specific intersection is to be designated as the intersection on which final alignment is to be based (which intersection is identifiable by a unique pattern at the intersection), the alignment intersection is centered properly in the field of view. When the wafer is thus properly aligned, the operator commands initiation of the learn mode by actuating the proper panel control. The system then realigns the wafer slightly so that its position agrees with that which would be generated by automatic coarse alignment, and presents a cursor, shown in FIG. 11 at 132, on the monitor display. Cursor 132 is generated by brightening a section of the horizontal scan on two horizontal scan lines by conventional circuitry (not shown). In the illustrated embodiment, these brightened sections are each 0.002 inch long and are spaced 0.001 inch apart along a 45° line.

As shown in FIG. 11, the field of view is considered to be divided into 8 octants, designated I through VIII. When the wafer is properly aligned, each octant contains a thoroughfare edge extending from the perpendicular intersection to an edge of the field of view. Now, using manual controls, which command circuitry well known to the art, the operator moves cursor 132 within one of the octants to straddle an edge which meets the criteria listed above. If no satisfactory edge exists within the octant, the operator commands cursor 132 to move to the next octant, etc., until he ultimately can choose an appropriate set of two edges, one of which is on a vertical thoroughfare and the other of which is on a horizontal thoroughfare. In practice, with reference to FIG. 11, edges 134, 136 are satisfactory edges for selection in octants I and II, respectively. But edges 138, 140 are part of features that are too narrow because slight horizontal positioning errors of the coarse alignment in the automatic mode could result in the use of an adjacent (wrong) edge instead of the memorized edge. Edges 142, 144 also are unsatisfactory because they do not extend far enough along the thoroughfare, so that positioning uncertainties of the coarse alignment could place these edges entirely outside of the field of view during fine alignment.

When the operator positions cursor 132 astride suitable edges and issues the appropriate command by operating a front panel control (not shown), the system memorizes the horizontal scan line numbers of the cursor pair, the positions of the cursor pair along their scan lines, and the position of the edge within the cursor. These six numbers (three for each cursor segment) for two cursor positions, one along a vertical thoroughfare, one along a horizontal thoroughfare, which uniquely define the position of the memorized corner to 0.0001 inch, are stored (by techniques well known in the art) by means of registers and counters synchronized with the television camera scan.

During the learn cycle, two other sequences of information are memorized as follows.

(1) Each quadrant containing a semiconductor device corner (i.e., the quadrants composed of octants II and III, IV and V, VI and VII, and VIII and I) is scanned to determine if the pattern of a recognizable unique device is present. If it is, the quadrant in which it is present is memorized and is used as a basis for choosing, from a stored program, the most efficient search scenario for the identification of the same unique device pattern is successive wafers during automatic operation.

(2) When such a pattern is found at the memorized intersection during the learn mode, the system control computer scans a front panel switch (not shown), which is set by the operator to indicate the appropriate class size of the pattern. The search routine for the alignment device can be optimized by incorporating this size information in the scenario used for the search.

After the learn mode is completed, the system is set in the automatic alignment mode, in which wafers are fed into the system, one at a time. The alignment procedure follows the scenario described above, with coarse alignments followed by fine alignment where appropriate. The fine alignment is implemented by establishing a search "window" which corresponds precisely with the position of cursor pair 132, chosen by the operator during the learn mode. If edges are found within this search window, they are tested to determine whether they lie along a 45° line. If they meet the 45° test, they are accepted as representing the pattern edges memorized and the X,Y,θ table is moved by appropriate commands, so as to position the selected edges at the memorized positions within the window. If no such edges are found, a search pattern for the window is generated, covering the entire area (0.003 inch×0.003 inch) of imprecision of the coarse alignment. If edges meeting the 45° test are found during the automatic alignment mode, the X,Y,θ table is moved by appropriate commands, until these edges first fall within the window corresponding to the memorized cursor position and then occupy the memorized position within this window.

THE DETAILED SCHEMATICS OF FIGS. 12 TO 18

Figure 12:
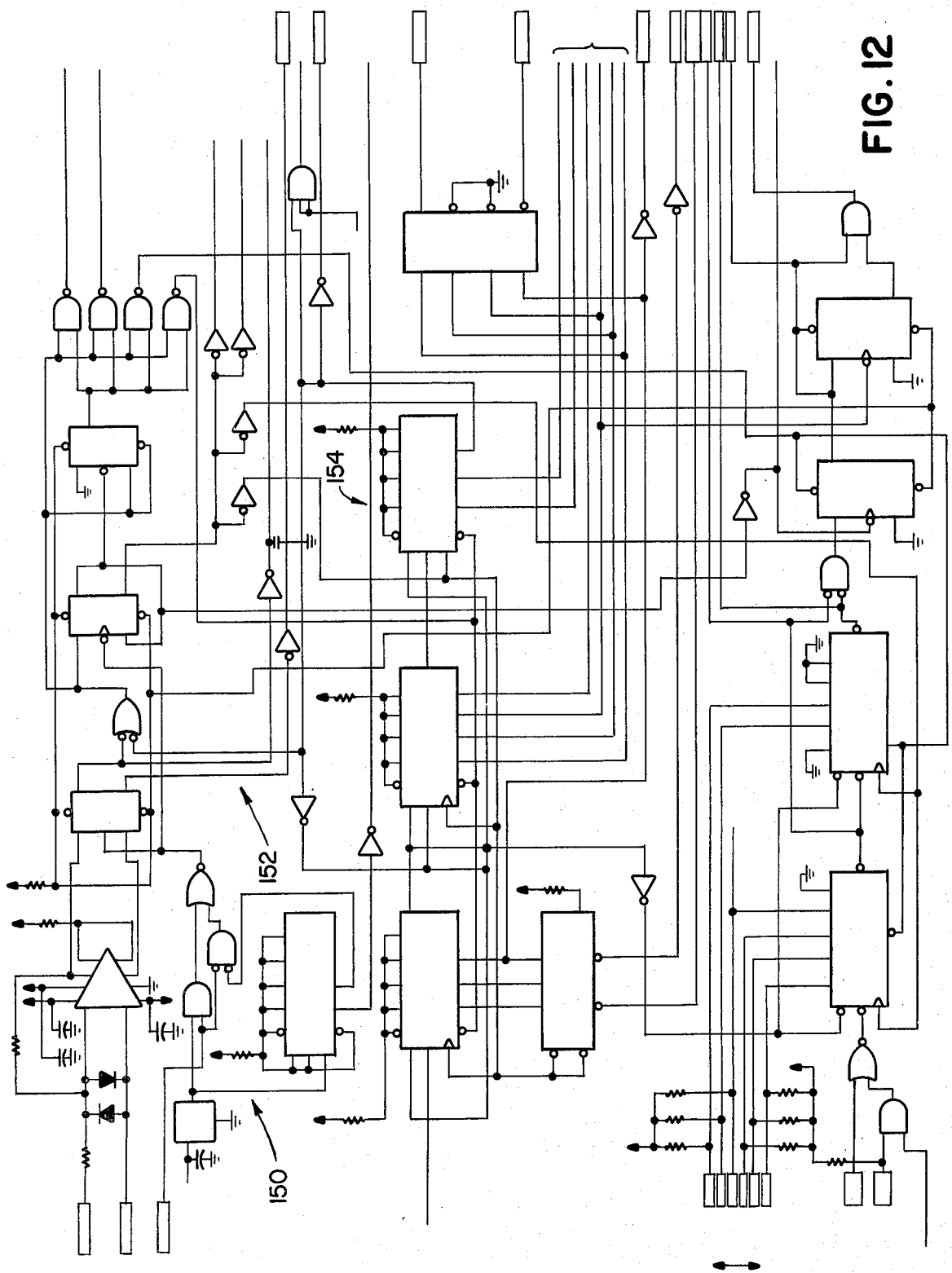
FIG. 12 is an electrical schematic of part of the timing circuitry of FIGS. 2 and 3.
Figure 13:
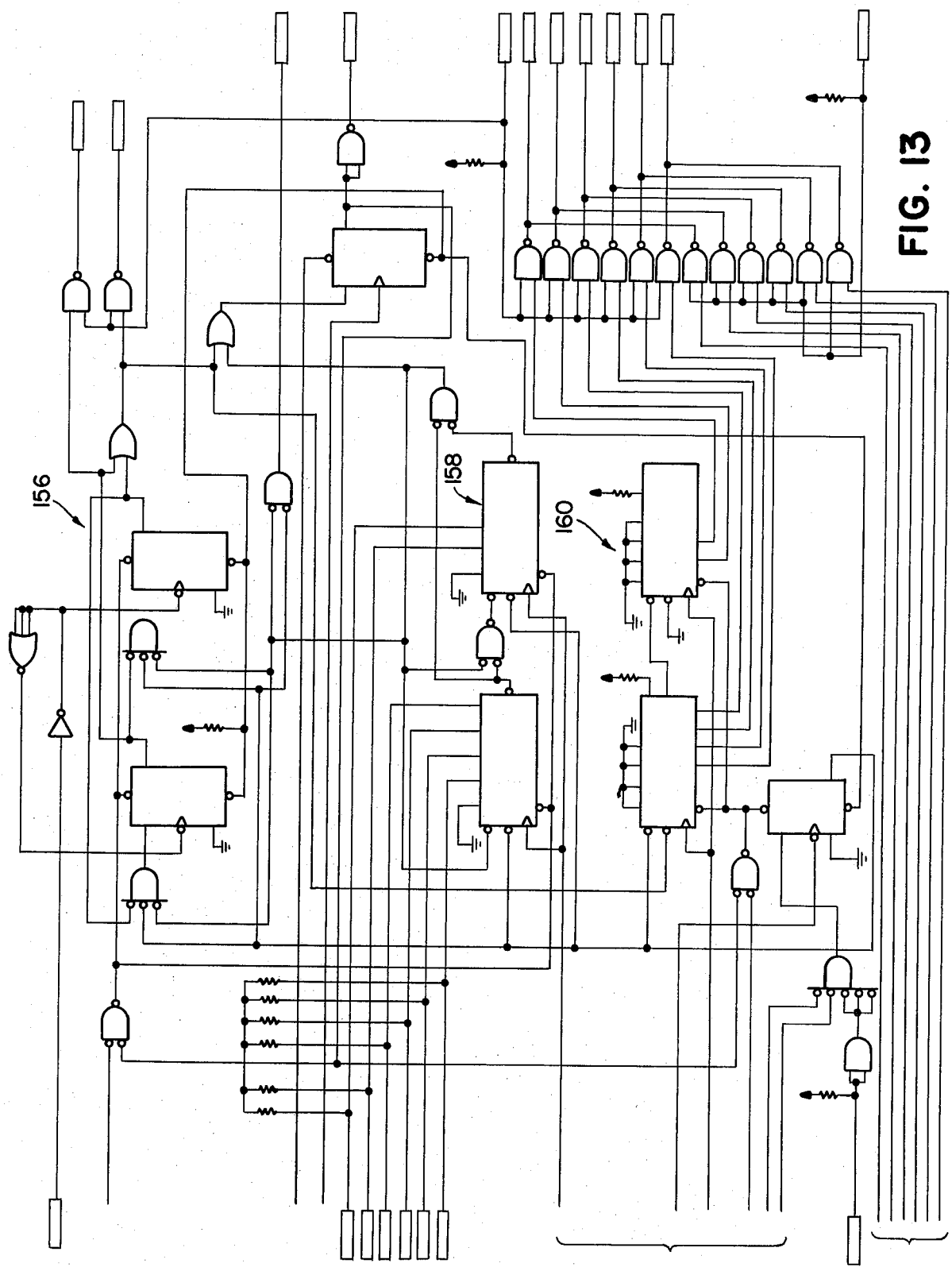
FIG. 13 is an electrical schematic of another part of the timing circuitry of FIGS. 2 and 3.
Figure 14:
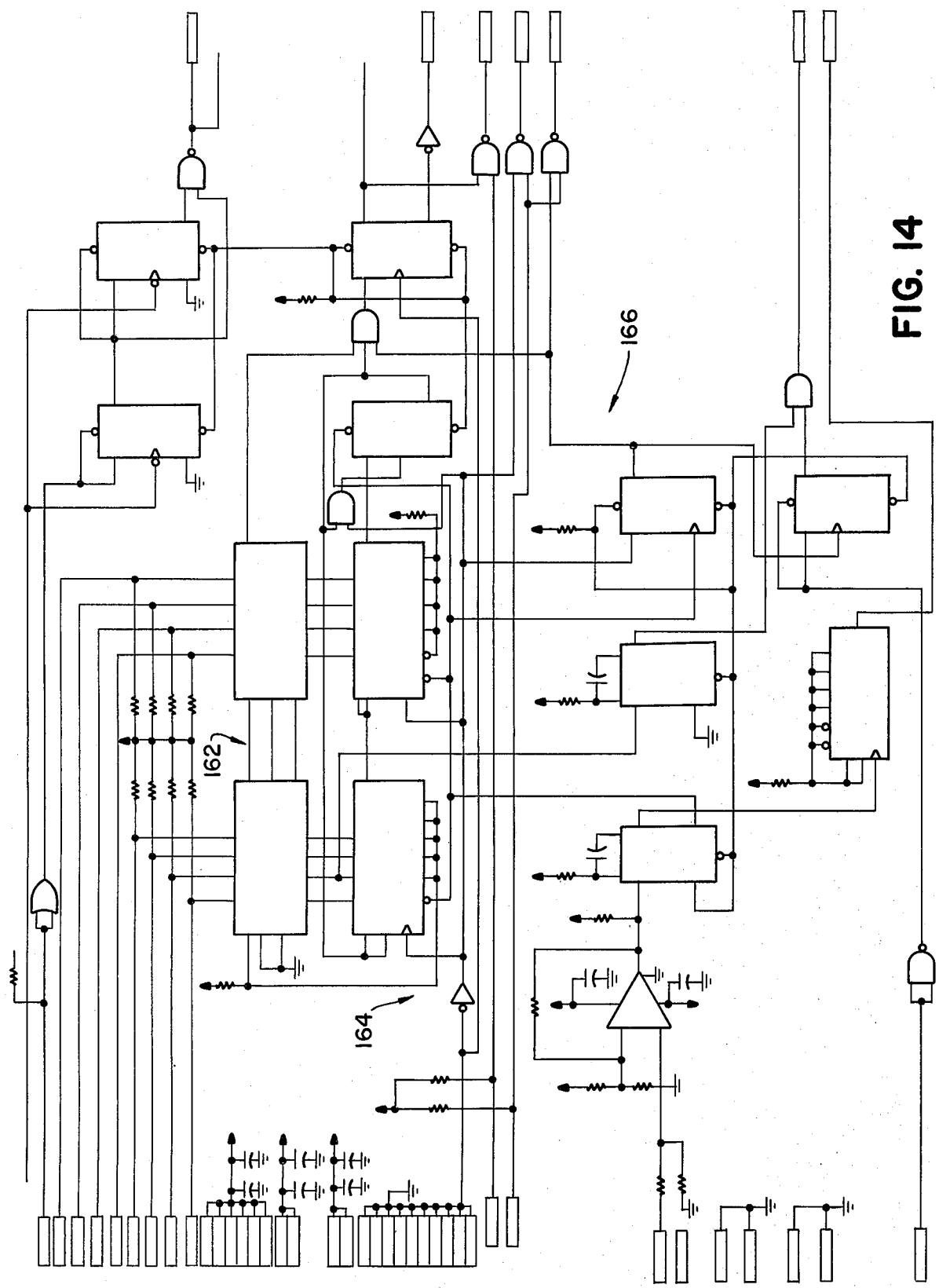
FIG. 14 is an electrical schematic of a further part of the timing circuitry of FIGS. 2 and 3.

FIGS. 12, 13 and 14 are more detailed schematics of the timing circuitry that synchronizes the operations of television camera 32, control sub-system 34, and television monitor 46. FIG. 12 shows clock pulse generator circuitry at 150, horizontal sync conditioner circuitry at 152, and coarse time slot counter circuitry at 154. FIG. 13 shows edge detection and reporting circuitry at 156, duration counter circuitry at 158, and edge position time slot counter circuitry at 160. FIG. 14 shows comparator circuitry at 162, starting time line counter circuitry at 164, and phase shifting circuitry at 166.

Figure 15:
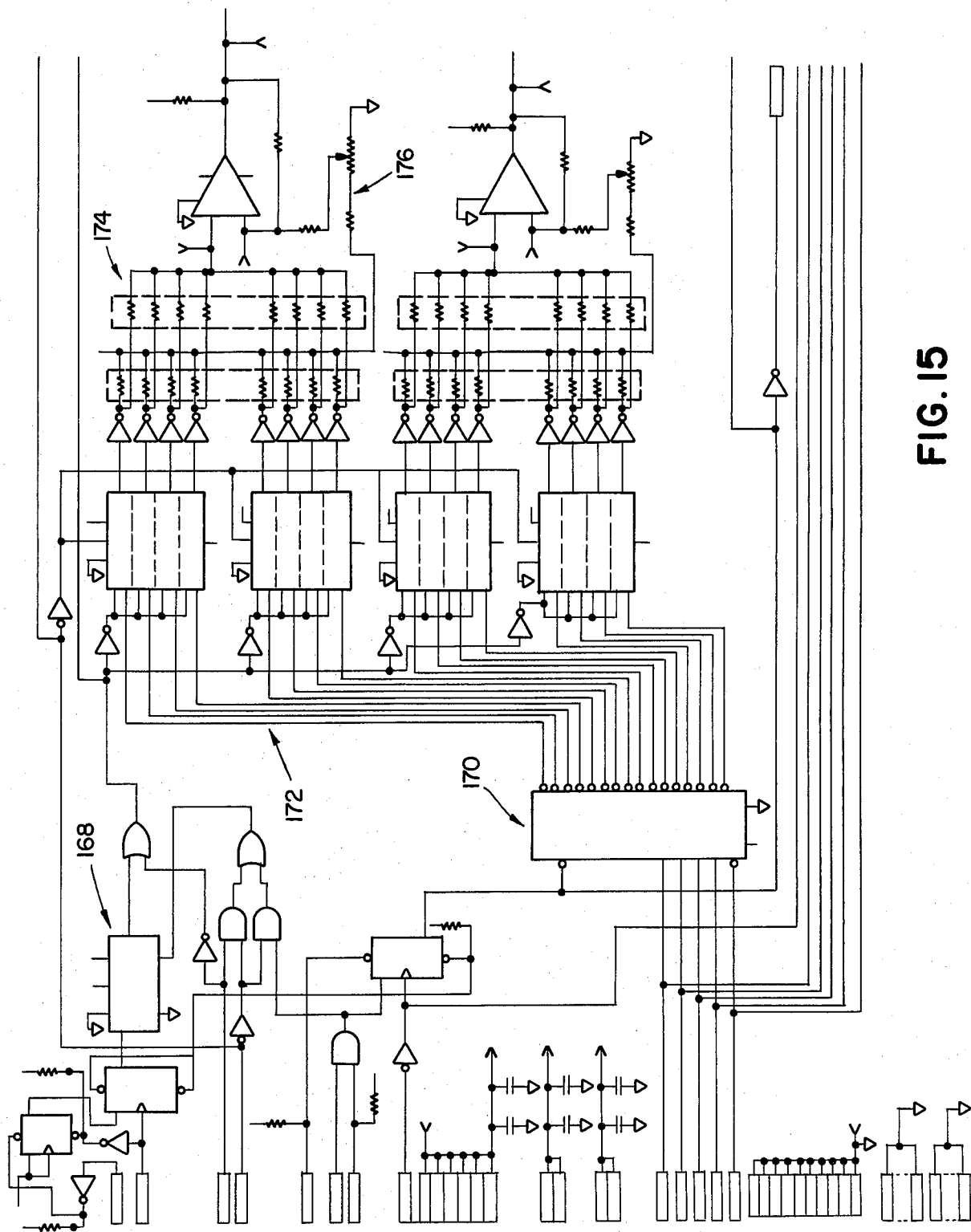
FIG. 15 is an electrical schematic of part of the correction circuitry of FIGS. 2 and 3.
Figure 16:
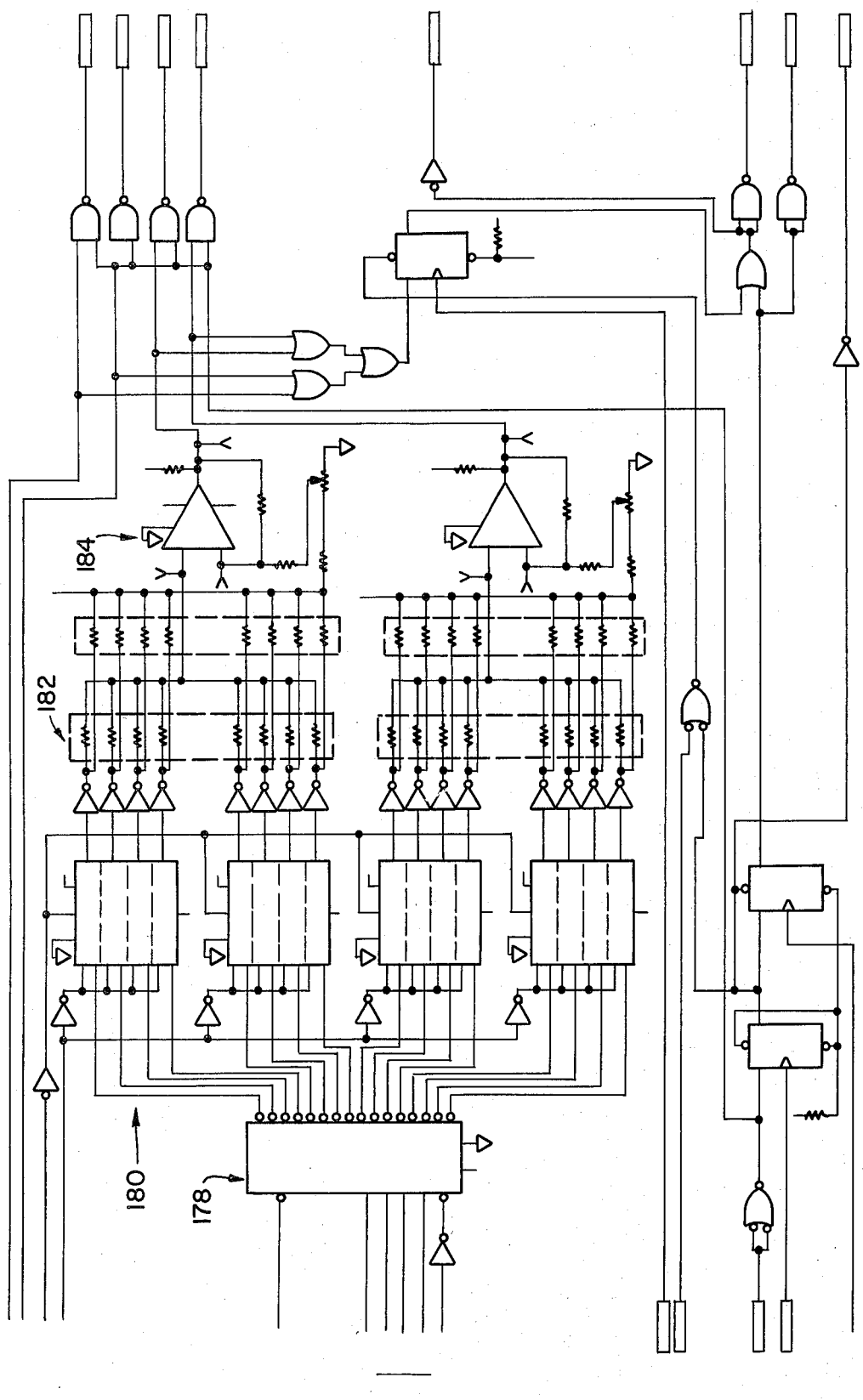
FIG. 16 is an electrical schematic of another part of the correction circuitry of FIGS. 2 and 3.

FIGS. 15 and 16 are more detailed schematics of the coarse memory. FIG. 15 shows phase shifting circuitry at 168, demultiplexing circuitry at 170, part of the coarse recirculating memory circuitry at 172, analog summer circuitry at 174, and threshold detector circuitry at 176. FIG. 16 shows demultiplexing circuitry at 178, part of the recirculating memory circuitry at 180, analog summer circuitry at 182, and threshold detector circuitry at 184.

Figure 17:
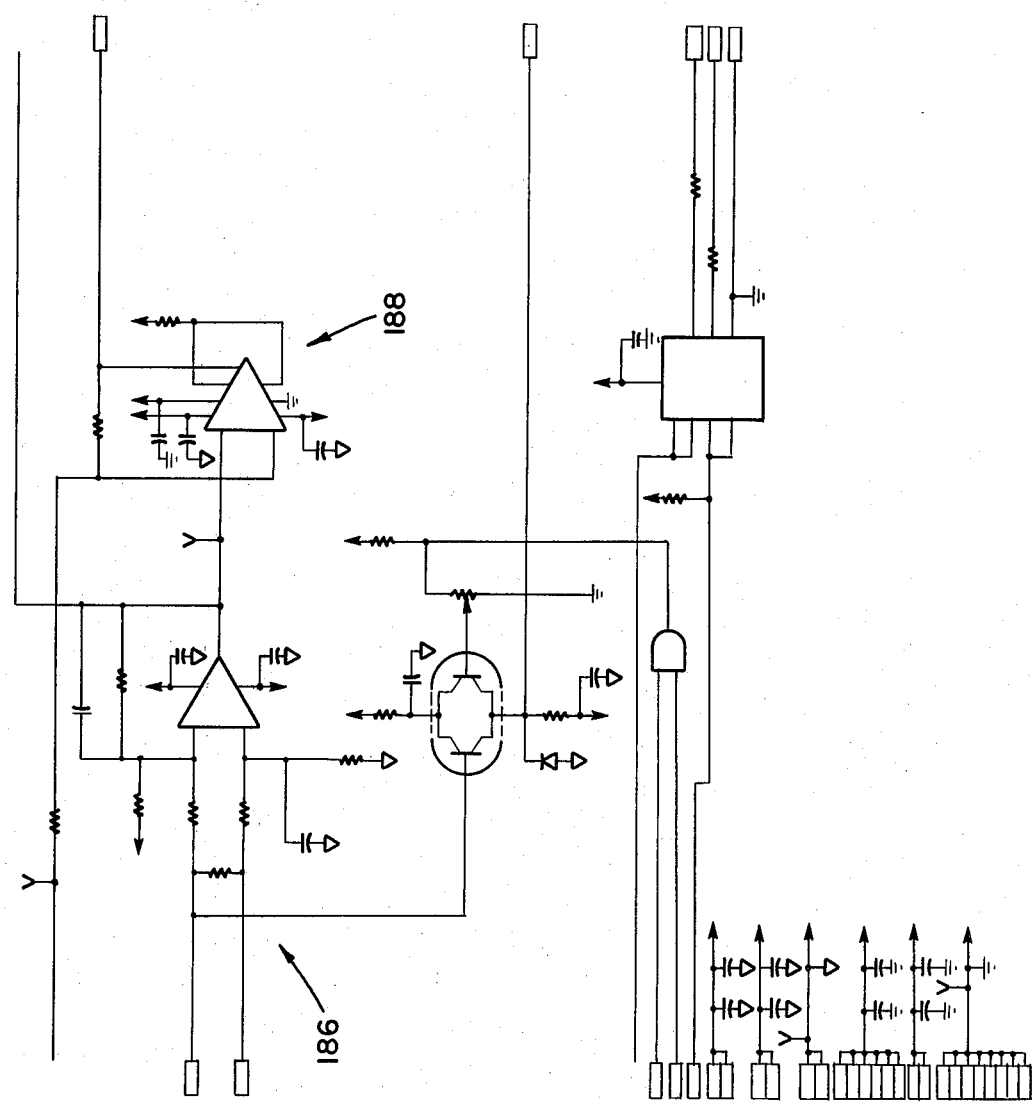
FIG. 17 is an electrical schematic of part of the video processor and output circuitry of FIGS. 2 and 3.

FIGS. 17 and 18 are more detailed schematics of the video processor and output circuitry. FIG. 17 shows camera video circuitry at 186 and video squarer circuitry at 188. FIG. 18 shows fine video level circuitry at 190, coarse video level circuitry at 192, and video level generation storage circuitry at 194.

SUMMARY OF OPERATION AND CONCLUSION

The present invention thus provides a system for aligning successive like semiconductor configurations, each characterized by a selected set of perpendicularly intersecting visual elements. In the illustrated example, the semiconductor configurations are wafers and the perpendicularly intersecting visual elements are spacings between individual devices, such spaces commonly being referred to as thoroughfares. Table 37 (FIG. 1), which adjustably carries and optically presents any one of the semiconductor configurations, includes conventional guides for constraining the table's motion in X, Y, and θ directions, and motors for driving the table in these directions. Television camera 32 is directed toward table 37 for viewing one of the successive semiconductor configurations on the table, the perpendicular visual elements of the semiconductor configuration being at 45° diagonals with respect to the raster scan coordinates of the television camera. Television monitor 46 displays the field viewed by camera 32. Pattern recognition and motor control circuitry 34 have two operating modes—an instruction mode and an automatic mode. During the instruction mode, an operator, viewing the television screen of monitor 46 and controlling the movement of table 37, examines one sample of the semiconductor configuration. The operator selects, as a reference, intersecting edges of perpendicularly intersecting visual elements and supervises the coarse and fine alignment procedures for predeterminedly positioning and orienting the reference elements' edges on the television screen and thereafter moves an electronic cursor to define two selected edges of the semiconductor configuration. When the operator has completed the instruction mode, the system is ready for operation in the automatic mode, in which each of a series of like semiconductor configurations are fed to table 37 for coarse and fine alignment with respect to the cursor without further intervention by the operator.

Since certain changes may be made in the present disclosure without departing from the invention hereof, it is intended that all matter shown in the accompanying drawings and described in the foregoing specification be interpreted in an illustrative and not in a limiting sense.

What is claimed is:

1. For use in a system for aligning successive like semiconductor configurations, each characterized by a set of perpendicularly intersecting visual elements, said system comprising table means for adjustably carrying and optically presenting any one of said semiconductor configurations, drive means for causing said table motions in X, Y, and θ directions, television camera means directed toward said table means for viewing any one of said semiconductor configurations on said table means, said television camera means being characterized by a raster of scan lines and producing pattern recognition signals corresponding to said scan lines, and television monitor means characterized by a raster of scan lines for displaying a representation of any one of said semiconductor configurations being carried on said table means:

(a) electronic control means operatively connected between said television camera means and said table means and between said television camera means and said television monitor means;
   (b) said electronic control means including memory means for storing representations of said pattern recognition signals;
   (c) manual supervision means for energizing said drive means in order to align a set of perpendicularly intersecting visual elements on a reference one of said semiconductor configurations, thereby generating reference pattern recognition signals and storing reference representations thereof in said memory means; and
   (d) automatic supervision means for comparing pattern recognition signals generated from a semiconductor configuration to be aligned on said table means and reference pattern recognition signals corresponding to said reference representations in said memory means, thereby energizing said drive means for aligning said set of perpendicular elements on said semiconductor configuration to be aligned.

2. The system of claim 1 wherein said pattern recognition signals include component signals representing of a plurality of band segments, each of said band segments corresponding to the traversal of one of said visual elements by a group of scan lines.

3. The system of claim 2 wherein said automatic supervision means includes coincidence means for determining the timing correspondence of said representations of said plurality of band segments in order to establish the identity of said one of said visual elements.

4. The system of claim 2 wherein said automatic supervision means includes decision means for establishing said identity by determining the timing correspondence of a predetermined number of said representations of said plurality of band segments.

5. The system of claim 1 wherein elements of said selected set of perpendicularly intersecting visual elements are oblique with respect to said raster of scan lines of said television camera means.

6. The system of claim 5 wherein elements of said selected set of perpendicularly intersecting visual elements are oblique with respect to said raster of scan lines of said television monitor means.

7. The system of claim 1 wherein elements of said selected set of perpendicularly intersecting visual elements are at 45° angles with respect to said raster of scan lines of said television camera means.

8. The system of claim 1 wherein elements of said selected set of perpendicularly intersecting visual elements are at 45° angles with respect to said raster of scan lines of said television monitor means.

9. The system of claim 2 wherein said electronic control means includes phase shifting means operately connected to said television camera means, and shift register means operatively connected to said phase shifting means, said phase shifting means processing said component signals into transformed signals representing said one of said visual elements in reoriented relation with respect to said raster of scan lines of said television camera, said shift register means establishing representations of said transformed signals for processing and transmission to said memory means.

10. The system of claim 2 wherein said electronic control means include phase shifting means operatively connected to said television camera means, shift register means operatively connected to said phase shifting means, analog summer means operatively connected to said shift register means, and threshold detector means operatively connected to said analog summer means, said phase shifting means processing said component signals into transformed signals representing said one of said visual elements in reoriented relation with respect to said raster of scan lines of said television camera, said shift register means establishing representations of said transformed signals for circulation thereof, said analog summer means combining transformed signals regenerated by said shift register means, said threshold detector means determining whether transformed signals combined by said summer means generate a summing signal that is greater or lesser than a predetermined level.

11. The system of claim 1 wherein said television camera means produces video signals in correspondence with said scan lines, said system comprising correction means for producing correction signals corresponding to said video signals, and threshold detector means for producing said pattern recognition signals in response to said correction signals and said video signals, said pattern recognition signals being quantized to two levels.

12. The system of claim 11 wherein said correction means includes analog-to-digital conversion means for producing digitized signals in response to said video signals, memory means for producing shading level signals in response to said digitized signals, and digital-to-analog conversion means for producing said correction signals in response to said shading level signals.

13. A system for aligning successive like semiconductor configurations, each characterized by a selected set of perpendicularly intersecting visual elements, said system comprising:
(a) table means for adjustably carrying and optically presenting any one of said semiconductor configurations, guide means for constraining said table means for motions in X, Y, and θ directions, and drive means for causing said motions;
(b) television camera means directed toward said table means for viewing any one of said semiconductor configurations on said table means, said television camera means being characterized by a raster of scan lines and producing pattern recognition signals corresponding to said scan lines;
(c) television monitor means characterized by a raster of scan lines for displaying a representation of any one of said semiconductor configurations being carried on said table means; and
(d) electronic control means operatively connected between said television camera means and said table means and between said television camera means and said television monitor means, said electronic control means including memory means for storing representations of said pattern recognition signals, manual supervision means for energizing said drive means in order to align a selected set of perpendicularly intersecting visual elements on a reference one of said semiconductor configurations, thereby generating reference pattern recognition signals and storing reference representations thereof in said memory means, and automatic supervision means for comparing selected pattern recognition signals corresponding to a selected semiconductor configuration on said table means and reference pattern recognition signals corresponding to said reference representations in said memory means, thereby energizing said drive means for aligning said selected set of perpendicularly intersecting elements on said selected semiconductor configuration.

14. The system of claim 13 wherein said pattern recognition signals include component signals representing of a plurality of band segments, each of said band segments corresponding to the traversal of one of said visual elements by a group of scan lines.

15. The system of claim 14 wherein said automatic supervision means includes coincidence means for determining the timing correspondence of said representations of said plurality of band segments in order to establish the identity of said visual elements.

16. The system of claim 14 wherein said automatic supervision means includes decision means for establishing said identity by determining the timing correspondence of a predetermined number of said representations of said plurality of band segments.

17. The system of claim 13 wherein elements of said selected set of perpendicularly intersecting visual elements are oblique with respect to said raster of scan lines of said television camera means.

18. The system of claim 17 wherein elements of said selected set of perpendicularly intersecting visual elements are oblique with respect to said raster of scan lines of said television monitor means.

19. The system of claim 13 wherein elements of said selected set of perpendicularly intersecting visual elements are at 45° angles with respect to said raster of scan lines of said television camera means.

20. The system of claim 19 wherein certain elements of said selected set of perpendicularly intersecting visual elements are at 45° angles with respect to said raster of scan lines of said television monitor means.

21. The system of claim 14 wherein said electronic control means includes phase shifting means operatively connected to said television camera means, and shift register means operatively connected to said phase shifting means, said phase shifting means processing said component signals into transformed signals representing said one of said visual elements in reoriented relation with respect to said raster camera, said shift register means establishing representations of said transformed signals for processing and transmission to said memory means.

22. The system of claim 14 wherein said electronic control means includes phase shifting means operatively connected to said television camera means, shift register means operatively connected to said phase shifting means, analog summer means operatively connected to said shift register means, and threshold detector means operatively connected to said analog summer means, said phase shifting means processing said component signals into transformed signals representing said one of said visual elements in reoriented relation with respect to said raster of scan lines of said television camera, said shift register means establishing representations of said transformed signals for circulation thereof, said analog summer means combining transformed signals regenerated by said shift register means, said threshold detector means determining whether transformed signals combined by said summer means generate a summing signal that is greater or lesser than a predetermined level.

23. The system of claim 13 wherein said television camera means produces video signals in correspondence with said scan lines, said system comprising correction means for producing corrections signals corresponding to said video signals, and threshold detector means for producing said pattern recognition signals in response to said correction signals and said video signals, said pattern recognition signals being quantized to two levels.

24. The system of claim 23 wherein said correction means includes analog-to-digital conversion means for producing digital signals in response to said video signals, memory means for producing shading level signals in response to said digital signals, and digital-to-analog conversion means for producing said correction signals in response to said shading level signals.

25. A system for utilizing X sensing means and Y sensing means at the center of an X,Y coordinate field for aligning a minute semiconductor configuration with respect to said center, said semiconductor configuration being characterized by a set of perpendicularly intersecting vertical and horizontal visual elements and being capable of X,Y and $\theta$ motions, said system comprising:
(a) means for commanding first X motion until a vertical visual element on an inner section of said configuration is sensed by said X sensing means;
(b) means for commanding first Y motion until an edge of said configuration is sensed by said Y sensing means;
(c) means for commanding first $\theta$ motion until X displacement, as sensed by said X sensing means, is corrected;
(d) means for commanding second Y motion, in the sense opposite that of said first Y motion, until a horizontal visual element is sensed by said Y sensing means;
(e) the intersection of selected vertical and horizontal visual elements thereby being centered coarsely;
(f) means for commanding third Y motion in the sense like that of said first Y motion, until said edge of said configuration is sensed by X sensing means;
(g) mens for commanding second $\theta$ motion until X displacement, as sensed by said X sensing means, is corrected;
(h) means for commanding fourth Y motion in the sense like that of said second Y motion, until said horizontal visual element is sensed by said Y sensing means;
(i) the intersection of said selected vertical and horizontal visual elements thereby being centered finely.

26. A system for aligning successive like semiconductor configurations with respect to a reference point in an X, Y coordinate field, each one of said configurations being characterized by a selected reference point at the intersection of generally perpendicularly related visual elements including a selected vertical element and a selected horizontal element, said system comprising:
(a) X, Y sensing means communicating with said X, Y coordinate field;
(b) X, Y, $\theta$ motion means for moving one of said configurations in said X, Y coordinate field; and
(c) control means operatively connected between said X, Y sensing means and said X, Y, $\theta$ motion means;
(d) said control means commanding X motion of said X, Y, $\theta$ motion means until said selected vertical visual element is sensed by said X, Y sensing means, said selected vertical element thereby being centered coarsely;
(e) said control means commanding a first relatively large Y motion of said X, Y, $\theta$ motion means until a selected edge of said one of said configurations is sensed by said X, Y sensing means, $\theta$ error thereby appearing as X displacement;
(f) said control means correcting said $\theta$ error by $\theta$ motion of said X, Y, $\theta$ motion means;
(g) said control means commanding a second relatively large Y motion of said X, Y, $\theta$ motion means in the sense opposite that of said first relatively large Y motion in order to return said reference point of said one of said configurations to the region of said reference point of said field of view;
(h) said control means commanding additional Y motion of said X, Y, $\theta$ motion means until said selected horizontal element is sensed by said X, Y sensing means, said selected reference point of said one of said configurations thereby being centered coarsely;
(i) said control means commanding a third relatively large Y motion of said X, Y, $\theta$ motion means until said selected edge is sensed by said X, Y sensing means;
(j) said control means commanding relatively fine Y motion and $\theta$ motion of said X, Y, $\theta$ motion means, thereby providing fine $\theta$ correction at said selected edge of said one of said configurations;
(k) said control means commanding a fourth relatively large Y motion of said X, Y, motion means in the sense opposite that of said third relatively large Y motion;
(l) said control means commanding additional Y motion until said selected horizontal element is sensed by said X, Y sensing means, whereby said selected reference point of said one of said configurations substantially coincides with said selected reference point of said field of view.

27. A process for aligning successive like semiconductor configurations with respect to a reference point in an X, Y coordinate field, each one of said configurations being characterized by a selected reference point at the intersection of generally perpendicularly related visual elements including a selected vertical element and a selected horizontal element, said system comprising X, Y sensing means communicating with said X, Y coordinate field, X, Y, $\theta$ motion means for moving one of said configurations in said X, Y coordinate field, and control means operatively connected between said X, Y sensing means and said X, Y, $\theta$ motion means, said process comprising the steps of:
(a) commanding, via said control means, X motion of said X, Y, $\theta$ motion means until said selected vertical visual element is sensed by said X, Y sensing means, said selected vertical element thereby being centered coarsely;
(b) commanding, via said control means, a first relatively large Y motion of said X, Y, $\theta$ motion means until a selected edge of said one of said configurations is sensed by said X, Y sensing means, $\theta$ error thereby appearing as X displacement;
(c) correcting, via said control means, said $\theta$ error by $\theta$ motion of said X, Y, $\theta$ motion means;
(d) commanding, via said control means, a second relatively large Y motion of said X, Y, $\theta$ motion means in the sense opposite that of said first relatively large Y motion in order to return said reference point of said one of said configurations to the region of said reference point of said field of view;

(e) commanding, via said control means, additional Y motion of said X, Y, θ motion means until said selected horizontal element is sensed by said X, Y sensing means, said selected reference point of said one of said configurations thereby being centered coarsely;

(f) commanding via said control means a third relatively large Y motion of said X, Y, θ motion means until said selected edge is sensed by said X, Y sensing means;

(g) commanding, via said control means, relatively fine Y motion and θ motion of said X, Y, θ motion means, thereby providing fine θ correction at said selected edge of said one of said configurations;

(h) commanding, via said control means, a fourth relatively large Y motion of said X, Y, θ motion means in the sense opposite that of said third relatively large Y motion;

(i) commanding, via said control means, additional Y motion until said selected horizontal element is sensed by said X, Y sensing means, whereby said selected reference point of said one of said configurations substantially coincides with said selected reference point of said field of view.

* * * * *